US012042540B2

(12) United States Patent
Mizutani et al.

(10) Patent No.: US 12,042,540 B2
(45) Date of Patent: Jul. 23, 2024

(54) FORMULATION COMPRISING ACTIVE PHARMACEUTICAL INGREDIENT

(71) Applicant: KANEKA CORPORATION, Osaka (JP)

(72) Inventors: Masaya Mizutani, Takasago (JP); Mitsuji Akazawa, Takasago (JP); Tatsuyoshi Tanaka, Takasago (JP); Hiroyuki Ogino, Takasago (JP)

(73) Assignee: KANEKA CORPORATION, Osaka (JP)

( * ) Notice: Subject to any disclaimer, the term of this patent is extended or adjusted under 35 U.S.C. 154(b) by 735 days.

(21) Appl. No.: 17/251,317

(22) PCT Filed: Jun. 13, 2019

(86) PCT No.: PCT/JP2019/023449
§ 371 (c)(1),
(2) Date: Dec. 11, 2020

(87) PCT Pub. No.: WO2019/240212
PCT Pub. Date: Dec. 19, 2019

(65) Prior Publication Data
US 2021/0260196 A1 Aug. 26, 2021

(30) Foreign Application Priority Data
Jun. 14, 2018 (JP) ................. 2018-113839

(51) Int. Cl.
| A61K 47/22 | (2006.01) |
| A61K 9/70 | (2006.01) |
| A61K 31/454 | (2006.01) |
| A61K 45/06 | (2006.01) |
| A61K 47/10 | (2017.01) |
| A61K 47/38 | (2006.01) |

(52) U.S. Cl.
CPC ............ *A61K 47/22* (2013.01); *A61K 9/7007* (2013.01); *A61K 31/454* (2013.01); *A61K 45/06* (2013.01); *A61K 47/10* (2013.01); *A61K 47/38* (2013.01)

(58) Field of Classification Search
CPC .... A61K 47/22; A61K 9/7007; A61K 31/454; A61K 45/06; A61K 47/10; A61K 47/38
USPC ....................................... 514/326
See application file for complete search history.

(56) References Cited

U.S. PATENT DOCUMENTS 4,691,013 A 9/1987 Sekimoto et al.
2004/0259732 A1 12/2004 Asrar et al.

FOREIGN PATENT DOCUMENTS

| CN | 105491997 A | 4/2016 | |
| CN | 105848719 A | 8/2016 | |
| JP | 2003-246733 A | 9/2003 | |
| JP | 2006347989 A | * 12/2006 | |
| JP | 2007-63136 A | 3/2007 | |
| JP | 2017-500374 A | 1/2017 | |
| JP | 2017-226623 A | 12/2017 | |
| WO | WO 03/105903 A1 | 12/2003 | |
| WO | WO 2015/077729 A2 | 5/2015 | |
| WO | WO 2015/077729 A3 | 5/2015 | |
| WO | WO-2017190070 A1 * | 11/2017 | ........... A61K 31/145 |
| WO | WO 2018/110693 A1 | 6/2018 | |

OTHER PUBLICATIONS

Japanese Notice of Reasons for Refusal for Japanese Application No. 2020-525647, dated Apr. 4, 2023, with an English translation.
Chinese Office Action and Search Report for Chinese Application No. 201980039977.5, dated May 31, 2023, with an English translation.
"Japanese Pharmaceutical Excipients Directory," Yakuji Nippo, Limited (1994), p. 235.
International Preliminary Report on Patentability and Written Opinion mailed Dec. 24, 2020, in PCT/JP2019/023449 (Forms PCT/IB/338, PCT/IB/373, and PCT/ISA/237.
International Search Report mailed Aug. 13, 2019, in PCT/JP2019/023449.
Japanese Office Action dated Jul. 25, 2023 for Application No. 2020-525647 with an English translation.
Chinese Office Action for Chinese Application No. 201980039977.5, dated Jan. 16, 2024, with an English translation.

* cited by examiner

*Primary Examiner* — Yih-Horng Shiao
(74) *Attorney, Agent, or Firm* — Birch, Stewart, Kolasch & Birch, LLP

(57) ABSTRACT

It is an object of the present invention to provide a formulation comprising ethyl cellulose, an active pharmaceutical ingredient, and a solvent, which is a stable formulation in which generation of impurities is suppressed even during the long-term storage. According to the present invention, provided is a formulation comprising (a) an active pharmaceutical ingredient, (b) ethyl cellulose, (c) 2-mercaptobenzimidazole, and (d) 0.1 part by weight or more of solvent with respect to 1 part by weight of the ethyl cellulose.

13 Claims, No Drawings

FORMULATION COMPRISING ACTIVE PHARMACEUTICAL INGREDIENT

TECHNICAL FIELD

The present invention relates to a formulation comprising an active pharmaceutical ingredient, which has good storage stability.

BACKGROUND ART

The dosage form of an external formulation includes a patch, an external liquid formulation, and a semi-solid formulation. Also, a film-forming formulation that is solidified after being applied to an affected area has been known. The aforementioned external formulation is prepared, for example, by mixing an active pharmaceutical ingredient, a solvent, and other components. In the case of preparing a semi-solid formulation or a film-forming formulation, a base polymer such as ethyl cellulose is used in some cases.

Meanwhile, the use of 2-mercaptobenzimidazole as an antioxidant or an oxidation inhibitor in pharmaceutical formulations has been known. For example, Patent Document 1 discloses an external formulation characterized by the mixing of urea and chlorobutanol therewith. This patent document discloses 2-mercaptobenzimidazole as one example of the antioxidant. In addition, Patent Document 2 discloses a solid composition comprising a nitrogen-containing condensed heterocyclic compound that is instable with oxygen. This patent document discloses 2-mercaptobenzimidazole as one example of the oxidation inhibitor. Moreover, Patent Document 3 discloses a nonaqueous patch, in which a non-steroidal anti-inflammatory drug is stably retained for a long period of time. This patent document discloses 2-mercaptobenzimidazole as one example of the oxidation inhibitor.

PRIOR ART DOCUMENTS

Patent Documents

Patent Document 1: Japanese Patent Publication (Kokai) No. 2007-63136 A
Patent Document 2: Japanese Patent Publication (Kokai) No. 2003-246733 A
Patent Document 3: Japanese Patent Publication (Kokai) No. 2017-226623 A

SUMMARY OF INVENTION

Object to be Solved by the Invention

In the research and development of a formulation comprising an active pharmaceutical ingredient, the present inventors have found that there is a case where impurities are generated during the long-term storage of a formulation comprising an active pharmaceutical ingredient, ethyl cellulose, and a solvent. It is an object of the present invention to provide a formulation comprising ethyl cellulose, an active pharmaceutical ingredient, and a solvent, which is a formulation having good storage stability, in which generation of impurities is suppressed even during the long-term storage.

Means for Solving the Object

The present inventors have conducted intensive studies directed towards achieving the aforementioned object. As a result, the inventors have found that 2-mercaptobenzimidazole is added to a formulation comprising an active pharmaceutical ingredient, ethyl cellulose, and a solvent, so that a formulation having good storage stability, in which generation of impurities is suppressed even during the long-term storage, can be provided. The present invention has been completed based on these findings.

Specifically, the present invention provides the following inventions.
<1> A formulation comprising:
  (a) an active pharmaceutical ingredient,
  (b) ethyl cellulose,
  (c) 2-mercaptobenzimidazole, and
  (d) 0.1 part by weight or more of solvent with respect to 1 part by weight of the ethyl cellulose.
<2> The formulation according to <1>, wherein the content of the active pharmaceutical ingredient is 0.1% by weight or more and 30% by weight or less.
<3> The formulation according to <1> or <2>, wherein the content of the ethyl cellulose is 0.1% by weight or more and 60% by weight or less.
<4> The formulation according to any one of <1> to <3>, wherein the content of the 2-mercaptobenzimidazole is 0.1% by weight or more and 10% by weight or less.
<5> The formulation according to any one of <1> to <4>, wherein the content of the solvent is 1% by weight or more and 90% by weight or less.
<6> The formulation according to any one of <1> to <5>, wherein the active pharmaceutical ingredient is a nitrogen atom-containing compound.
<7> The formulation according to <6>, wherein the nitrogen atom-containing compound is a compound comprising an open-chain amine structure or a cyclic amine structure.
<8> The formulation according to <6> or <7>, wherein the nitrogen atom-containing compound is a compound comprising an open-chain tertiary amine structure, a cyclic tertiary amine structure, or a cyclic amine structure having an aromatic ring.
<9> The formulation according to any one of <1> to <8>, wherein the active pharmaceutical ingredient is efinaconazole or a salt thereof.
<10> The formulation according to any one of <1> to <5>, wherein the active pharmaceutical ingredient is an oxygen atom-containing compound.
<11> The formulation according to <10>, wherein the oxygen atom-containing compound is a compound comprising a hydroxyl group, a carbonyl group, or an ether group.
<12> The formulation according to <10> or <11>, wherein the oxygen atom-containing compound is a compound comprising a cyclic alcohol structure, a cyclic carbonyl structure or a cyclic ether structure.
<13> The formulation according to any one of <1> to <5>, wherein the active pharmaceutical ingredient is a sulfur atom-containing compound.
<14> The formulation according to any one of <1> to <13>, further comprising organic acid.
<15> The formulation according to any one of <1> to <14>, wherein the solvent is at least one solvent selected from the group consisting of esters, alcohols, nitrogen-containing compounds, terpenes, oils, ketones, ethers, and water.
<16> The formulation according to any one of <1> to <15>, wherein the solvent is at least one solvent selected from the group consisting of ethanol, isopropanol, ethyl acetate, water, isopropyl myristate, octyldodecyl myristate, diisopropyl adipate, diethyl sebacate, cetyl 2-ethylhexanoate (cetyl isooctanoate), hexadecyl isostearate, triethyl citrate, isostearyl alcohol, lauryl alcohol, 2-octyldodecanol, 2-hexyldecanol, oleyl alcohol, propylene glycol, 1,3-butanediol, propylene glycol monocaprylate, diethylene glycol monoethyl ether, polyethylene glycol, N-methyl-2-pyrrolidone, and liquid paraffin.

<17> The formulation according to any one of <1> to <16>, which is a liquid formulation or a semi-solid formulation.
<18> The formulation according to <17>, which is a film-forming formulation that is solidified after being applied to an affected area.

Advantageous Effects of Invention

According to the present invention, there can be provided a formulation comprising ethyl cellulose, an active pharmaceutical ingredient, and a solvent, which is a formulation having good storage stability, in which generation of impurities is suppressed even during the long-term storage.

Embodiment of Carrying Out the Invention

Hereinafter, the present invention will be described in detail.

The present application claims the benefit of priority from Japanese Patent Application No. 2018-113839, filed on Jun. 14, 2018. The entire content of the description of Japanese Patent Application No. 2018-113839, filed on Jun. 14, 2018, is hereby incorporated by reference.

The formulation of the present invention is a formulation comprising (a) an active pharmaceutical ingredient, (b) ethyl cellulose, (c) 2-mercaptobenzimidazole, and (d) 0.1 part by weight or more of solvent with respect to 1 part by weight of the ethyl cellulose.

(a) Active Pharmaceutical Ingredient

The active pharmaceutical ingredient used in the present invention may be, but is not particularly limited to, a nitrogen atom-containing compound, an oxygen atom-containing compound, or a sulfur atom-containing compound. The active pharmaceutical ingredient is preferably a nitrogen atom-containing compound or an oxygen atom-containing compound, and is more preferably a nitrogen atom-containing compound.

The nitrogen atom-containing compound may be a compound comprising an open-chain amine structure or a compound comprising a cyclic amine structure.

The open-chain amine structure may be, but is not particularly limited to, an open-chain primary amine structure, an open-chain secondary amine structure, or an open-chain tertiary amine structure.

The cyclic amine structure may be, but is not particularly limited to, a cyclic secondary amine structure, a cyclic tertiary amine structure, an aromatic ring, or an imine and/orenamine structure in a ring structure.

Specific examples of the nitrogen atom-containing compound are shown below.

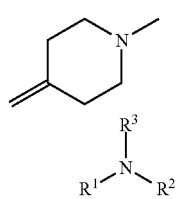

[Formula 1]

(wherein $R^1$, $R^2$ and $R^3$ each represent any given atom or atomic group)

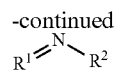

(wherein $R^1$ and $R^2$ each represent any given atom or atomic group)

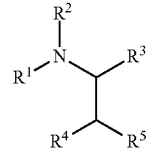

(wherein $R^1$ to $R^5$ each represent any given atom or atomic group)

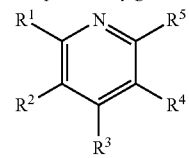

(wherein $R^1$ to $R^5$ each represent any given atom or atomic group)

Examples of the atom represented by each of the above-described $R^1$ to $R^5$ may include, but are not particularly limited to, hydrogen, deuterium, nitrogen, oxygen, fluorine, chlorine, bromine, and iodine. An example of the atomic group represented by each of the above-described $R^1$ to $R^5$ may be, but is not particularly limited to, an atomic group consisting of an alkyl group, an alkenyl group, an alkynyl group, an aryl group, an amino group, a hydroxyl group, an aldehyde group, a ketone group, a carboxyl group, an ester group, an ether group, an amide group, a sulfo group, a thiol group, a cyano group, a nitro group, a halogen-containing side chain, and a combination thereof.

The oxygen atom-containing compound may be, but is not particularly limited to, a compound comprising an ether group, a compound comprising a hydroxyl group, or a compound comprising a carbonyl group. More specific examples of the oxygen atom-containing compound may include, but are not particularly limited to, a compound comprising a cyclic ether structure, a compound comprising an open-chain ether structure, a compound comprising a cyclic alcohol structure, a compound comprising an open-chain alcohol structure, a compound comprising a cyclic carbonyl structure, and a compound comprising an open-chain carbonyl structure.

Specific examples of the oxygen atom-containing compound are shown below.

[Formula 2]

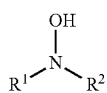

($R^1$ and $R^2$ each represent any given atom or atomic group)

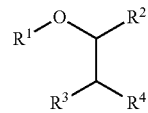

($R^1$ to $R^4$ each represent any given atom or atomic group)

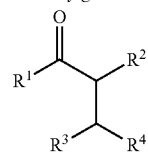

($R^1$ to $R^4$ each represent any given atom or atomic group)

Examples of the atom represented by each of the above-described $R^1$ to $R^4$ may include, but are not particularly limited to, hydrogen, deuterium, nitrogen, oxygen, fluorine, chlorine, bromine, and iodine. An example of the atomic group represented by each of the above-described $R^1$ to $R^4$ may be, but is not particularly limited to, an atomic group consisting of an alkyl group, an alkenyl group, an alkynyl group, an aryl group, an amino group, a hydroxyl group, an aldehyde group, a ketone group, a carboxyl group, an ester group, an ether group, an amide group, a sulfo group, a thiol group, a cyano group, a nitro group, a halogen-containing side chain, and a combination thereof.

The sulfur atom-containing compound may be, but is not particularly limited to, a compound comprising a thioether group, a compound comprising a thiol group, or a compound comprising a thiocarbonyl group. More specific examples of the sulfur atom-containing compound may include, but are not particularly limited to, a compound comprising a cyclic thioether structure, a compound comprising an open-chain thioether structure, a compound comprising a cyclic thiol structure, a compound comprising an open-chain thiol structure, a compound comprising a cyclic thiocarbonyl structure, and a compound comprising an open-chain thiocarbonyl structure.

Among the nitrogen atom-containing compounds, examples of the compound comprising an open-chain primary amine structure may include, but are not limited to, mitodrine, noradrenaline, dopamine, methyldopa, levodopa, carbidopa, droxidopa, alendronic acid, kanamycin, tobramycin, oseltamivir, zanamivir, peramivir, laninamivir, doxorubicin, GABA, gabapentin, pregabalin, amantadine, memantine, benzocaine, ethenzamide, salicylamide, tranexamic acid, and fluvoxamine.

Among the nitrogen atom-containing compounds, examples of the compound comprising an open-chain secondary amine structure may include, but are not limited to, ephedrine, ritodrine, adrenaline, etilefrine, phenylephrine, zipibefrine, procaterol, fenoterol, tulobuterol, salmeterol, salbutamol, acebutolol, atenolol, carteolol, metoprolol, pindolol, propranolol, timolol, bisoprolol, labetalol, sotalol, carvedilol, sulpiride, tiapride, mosapride, tamsulosin, furosemide, torasemide, bumetanide, diclofenac, mefenamic acid, tranilast, glibenclamide, gliclazide, glimepiride, glyclopyramide, nateglinide, voglibose, nafamostat, streptomycin, vancomycin, gentamicin, ozogamycin, teicoplanin, capsaicin, safinamide, actalit, acetophenone, atomoxetine, ampicillin, ambroxol, isoprenaline, colchicine, sertraline, ramelteon, and maprotiline.

Among the nitrogen atom-containing compounds, examples of the compound comprising an open-chain tertiary amine structure may include, but are not limited to, lidocaine, dibucaine, prlocaine, procaine, tetracaine, oxybuprocaine, distigmine, neostigmine, pyridostigmine, ribastigmine, verapamil, selegiline, nifecalant, amiodarone, captopril, lisinopril, enalapril, imidapril, temocapril, salpogrelate, olopatadine, bromhexine, mitiglinide, repaglinide, metformin, buformin, tamoxifen, clomiphene, toremifene, josamycin, erythromycin, clarithromycin, rotigotine, ropinirole, oxybutynin, metoclopramide, entacapone, tramadol, amitriptyline, crotamiton, diphenhydramine, tolterodine, tropicamide, butenafine, milnacipran, and chlorpheniramine.

Among the nitrogen atom-containing compounds, examples of the compound comprising a cyclic secondary amine structure may include, but are not limited to, naphazoline, oxymetazoline, tramazoline, tetrahydrozoline, tolazoline, cibenzoline, nifedipine, nicardipine, amlodipine, cilnidipine, felodipine, barbital, phenobarbital, phenytoin, ethotoin, clonidine, argatroban, hydrochlorothiazide, efavirenz, crizotinib, methylphenidate, vanicrene, paroxetine, duloxetine, trichlormethiazide, and faszil.

Among the nitrogen atom-containing compounds, examples of the compound comprising a cyclic tertiary amine structure may include, but are not limited to, efinaconazole, itraconazole, ketoconazole, mepivacaine, bupivacaine, ropivacaine, cocaine, reserpine, sildenafil, vardenafil, minoxidil, trapidil, urapidil, bepridil, naftopidil, flumazenil, perospirone, tandospirone, morphine, dextromethorphan, buprenorphine, apomorphine, naloxone, fentanyl, butyrophenones such as spiperone and timiperone, risperidone, domperidone, aripiprazole, imipramine, clocaplamin, blonanserin, mianserin, aprepitant, azimarin, flecainide, pilsicainide, bunazocin, prazosin, clopidogrel, indapamide, mozabaptane, tolvaptan, phenylbutazone, piroxicam, meloxicam, emedastine, cyproheptadine, cetirizine, tacrolimus, everolimus, temsirolimus, azasetron, palonosetron, alogliptin, sitagliptin, teneligliptin, linagliptin, vildagliptin, anagliptin, raloxifene, enoxacin, norfloxacin, ofloxacin, gatifloxacin, levofloxacin, lincomycin, clindamycin, mitomycin C, rifampicin, mikafungin, indinavir, nelfinavir, saquinavir, estramstin, irinotecan, methotrexate, vinblastine, vincristine, imatinib, gefitinib, nicotin, donepezil, scopolamine, lurasidone, asenapine, galantamine, talipexole, biperiden, trihexyphenidyl, prophenamine, metixene, atropine, homatropine, octatropine, trihexyphenidyl, haloperidol, clemastine, azithromycin, azimarin, amorolfine, epinastine, ebastine, oxatomid, oxycodone, clomipramine, chlorpromazine, silodosin, solifenacin, tadalafil, tipepidine, ticlopidine, doxapram, trazodone, trimipramine, trimethadione, trimetazidine, tolvaptan, pilsicainide, pyroheptin, mazindol, loratadine, setiptiline, promethazine, alimemazine, dipyridamole, diracep, sparfloxacin, lomefloxacin, and tosufloxacin.

Among the nitrogen atom-containing compounds, examples of the compound having a cyclic amine which contains aromatic structure or imine and/or enamine structure may include, but are not limited to, papaverine, bosentan, hepronicart, inositol hexanicotinate, zolpidem, zopiclone, rilmazafone, diazepam, fludiazepam, flunitrazepam, prazepam, oxazolam, midazolam, oxazolam, bromazepam, clonazepam, nitrazepam, lysergic acid, ergotamine, ergometrine, cabergoline, pergolide, pirenzepine, carbamazepine, amoxapine, quetiapine, olanzapine, clozapine, mirtazapine, caffeine, theophylline, aminophylline, sumatriptan, zolmitriptan, pimobendan, disopyramide, candesartan, losartan, olmesartan, telmisartan, valsartan, irbesartan, azilsartan, guanabens, ozagrel, etdrak, selecoxib, indomethacin, acemethacin, azelastine, cimetidine, famotidine, nizatidine, ranitidine, lafutidine, ibudilast, montelukast, planscast, imiquimod, granisetron, indicetron, ondansetron, ramosetron, tropisetron, omeprazole, rabeprazole, lansoprazole, esomeprazole, pioglitazone, atorvastatin, fluvastatin, pitavastatin, rosuvastatin, risedronic acid, zoledronic acid, sulfamethoxazole, sulfamethoxyn, trimethoprim, synoxacin, tazobactam, breomycin, metronidazole, miconazole, fluconazole, econazole, fosfluconazole, lanoconazole, luriconazole, neticonazole, oxiconazole, sulconazole, voriconazole, cyclopyrox, abacavir, entecavir, acyclovir, ganciclovir, tenofovir, ritonavir, raltegravir, dolutegravir, ribavirin, mebendazole, nimustin, camptothecin, cytarabine, gemcitabine, capecitabine, enocitabine, dimivudine, lamivudine, fluorouracil, gimeracil, oteracil, anastrozole, letrozole, pramipexole, zonisamide, peranpanel, actinomycin D, acetazolamide, adenosine, aldioxa, alprazolam, allopurinol, isoniazid, imidafenacin, etizolam, salazosulfapyridine, and triamterene.

Among the oxygen atom-containing compounds, examples of the compound comprising a cyclic ether structure may include, but are not limited to, ivermectin and isosorbide.

Among the oxygen atom-containing compounds, examples of the compound comprising a cyclic alcohol structure may include, but are not limited to, calcitriol, alfacalcidol, estradiol, estriol, ethinyl estradiol, norgestrel-ethinyl estradiol, and ethinyl estradiol-levonorgestrel.

Among the oxygen atom-containing compounds, an example of the compound comprising an open-chain alcohol structure may be, but is not limited to, retinol.

Among the oxygen atom-containing compounds, examples of the compound comprising an open-chain carbonyl structure may include, but are not limited to, felbinac, sulindac, fenbufen, ibuprofen, flurbiprofen, ketoprofen, loxoprofen, crofibrate, bezafibrate, phenofibrate, pravastatin, tretinoin, dinoprost, and aspirin.

Among the oxygen atom-containing compounds, examples of the compound comprising a cyclic carbonyl structure may include, but are not limited to, spironolactone, hydrocortisone, fludroxycortide, prednisolone, methylprednisolone, beclomethasone propionic acid ester, betamethasone, dexamethasone, budesonide, cromoglycic acid, simvastatin, progesterone, norgestrel, testosterone, methyltestosterone, fluorosinolone, triamcinolone, methenolone, minocycline, doxycycline, tetracycline, daunorubicin, paclitaxel, docetaxel, alprostadil, limaprost, menatetrenone, and ubidecarenone.

Examples of the sulfur atom-containing compounds may include, but are not limited to, cevimeline, diltiazem, benzylpenicillin, amoxicillin, bacampicillin, sultamicillin, faropenem, imipenem, meropenem, cephalexin, cefazolin, cefadroxil, cefaclor, cefotiam, cefdinir, and latamoxef.

In the case of the above-described active pharmaceutical ingredients that are in free forms, salts thereof can be used, and free-form salts can also be used.

In one example of the present invention, efinaconazole can be used among the above-described pharmaceutical ingredients.

Efinaconazole that can be used in the present invention may be either free-form efinaconazole, or a pharmaceutically acceptable salt of efinaconazole. Efinaconazole is also referred to as KP-103 or (2R,3R)-2-(2,4-difluorophenyl)-3-(4-methylenepiperidin-1-yl)-1-(1H-1,2,4-triazol-1-yl)butan-2-ol. The pharmaceutically acceptable salt thereof is not particularly limited, and it may be either an inorganic salt or an organic salt. Examples of the inorganic salt of efinaconazole may include hydrochloride, hydrobromide, nitrate, sulfate, and phosphate. Examples of the organic salt of efinaconazole may include formate, acetate, trifluoroacetate, propionate, lactate, tartrate, oxalate, fumarate, maleate, citrate, malonate, methane sulfonate, and toluene sulfonate. From the viewpoint of availability, free-form efinaconazole is preferably used.

As such efinaconazole or a salt thereof, those produced by a known method can be used, or commercially available products satisfying the above-described characteristics of efinaconazole can also be used. Moreover, efinaconazole is commercially available, and can be purchased from, for example, Sigma-Aldrich Japan (product code: SML1244).

In order to obtain sufficient medicinal effects, the content of the active pharmaceutical ingredient (for example, efinaconazole) is preferably 0.1% by weight or more, more preferably 0.5% by weight or more, and further preferably 1% by weight or more, with respect to the total amount of the formulation components. On the other hand, from the viewpoint of suppression of precipitation of drug crystals in the formulation, the upper limit of the content of the active pharmaceutical ingredient is preferably 30% by weight or less, more preferably 25% by weight or less, further preferably 20% by weight or less, particularly preferably 15% by weight or less, and most preferably 10% by weight or less.

(b) Ethyl Cellulose

Ethyl cellulose that can be used in the formulation of the present invention is not particularly limited, as long as it is ethyl cellulose in which the hydrogen atom (H) of the hydroxyl group (OH group) of cellulose is substituted with an ethyl group (C2H5). In the present description, the ratio of the hydrogen atoms of the hydroxyl groups substituted with ethyl groups in the ethyl cellulose is referred to as "ethyl group substitution percentage."

The ethyl group substitution percentage is not particularly limited, and it may be 10% or more, 20% or more, 30% or more, 40% or more, or 45% or more. On the other hand, the ethyl group substitution percentage may also be 100%, 90% or less, 80% or less, 70% or less, 60% or less, or 55% or less. From the viewpoint of solubility in the solvent, the ethyl group substitution percentage is preferably 30% or more and 70% or less, more preferably 40% or more and 60% or less, and further preferably 45% or more and 55% or less.

The weight average molecular weight (MW) of ethyl cellulose is not particularly limited, and it may be 20000 or more, 40000 or more, or 60000 or more. On the other hand, the weight average molecular weight (MW) of ethyl cellulose may also be 400000 or less, 300000 or less, or 230000 or less. When the present invention is applied as a coating agent, the weight average molecular weight of ethyl cellulose and the content of ethyl cellulose to the total amount of the formulation components are appropriately selected, so that a formulation having a viscosity that provides easy applicability can be obtained.

With regard to the ethyl cellulose used in the present invention, one type of ethyl cellulose may be used, or two or more types of ethyl celluloses each having a different ethyl group substitution percentage or a different weight average molecular weight may be combined with one another.

In a certain example of the present invention, if the ethyl group substitution percentage in ethyl cellulose is low, there may be a case where the ethyl cellulose is not dissolved in the solvent, causing gelatinization, etc. On the other hand, in another example of the present invention, if the ethyl group substitution percentage is high, there may be a case where the ethyl cellulose is not dissolved in the solvent.

In one example of using the present invention as a coating agent, if the weight average molecular weight of ethyl cellulose is low, there may be a case where a sufficient viscosity cannot be provided to the formulation and thus, the coating agent is hardly applied. In another example of the present invention, if the weight average molecular weight of ethyl cellulose is high, there may be a case where the formulation gets hard and thus, is hardly applied.

Ethyl cellulose produced by a known method can be used, or commercially available products satisfying the above-described characteristics of ethyl cellulose can also be used. Moreover, ethyl cellulose is commercially available, and examples of the commercially available ethyl cellulose may include: "ETHOCEL STD4," "ETHOCEL STD7," "ETHOCEL STD10," "ETHOCEL STD20," "ETHOCEL STD45," "ETHOCEL STD100," "ETHOCEL STD200," "ETHOCEL STD300," "ETHOCEL MED50," and "ETHOCEL MED70," which are manufactured by The Dow Chemical;

and "T10 Pharm," "N7 Pharm," "N10 Pharm," "N14 Pharm," "N22 Pharm," "N50 Pharm," and "N100 Pharm," which are manufactured by Ashland.

The content of the ethyl cellulose to the total amount of the formulation components is not particularly limited, as long as it is in a range that does not impair the form of the formulation. In one example of the present invention, the lower limit of the content of the ethyl cellulose is preferably 0.1% by weight or more, more preferably 1% by weight or more, and may also be 5% by weight or more or 7% by weight or more, with respect to the total amount of the formulation components. The upper limit of the content of the ethyl cellulose is preferably 60% by weight or less, and may also be 50% by weight or less, 40% by weight or less, 30% by weight or less, 20% by weight or less, or 15% by weight or less, with respect to the total amount of the formulation components.

(c) 2-Mercaptobenzimidazole

The use of 2-mercaptobenzimidazole as an antioxidant in formulations has conventionally been known. In the present invention, it has been found that 2-mercaptobenzimidazole suppresses generation of impurities in a formulation comprising an active pharmaceutical ingredient, ethyl cellulose, and a solvent, during the long-term storage. When an antioxidant other than 2-mercaptobenzimidazole was used, it did not exhibit the effect of suppressing generation of impurities in the formulation during the long-term storage. Accordingly, the above-described effect of the present invention could not be predicted from 2-mercaptobenzimidazole used as an antioxidant, and thus, this effect was totally unexpected.

The content of 2-mercaptobenzimidazole to the total amount of the formulation components is not particularly limited, as long as it is in a range that does not impair the effects of the present invention. The lower limit of the content of the 2-mercaptobenzimidazole is preferably 0.01% by weight or more, more preferably 0.05% by weight or more, particularly preferably 0.1% by weight or more, and may also be 0.2% by weight or more or 0.5% by weight or more, with respect to the total amount of the formulation components. The upper limit of the content of the 2-mercaptobenzimidazole is preferably 10% by weight or less, more preferably 8% by weight or less, and most preferably 5% by weight or less, with respect to the total amount of the formulation components.

(d) Solvents

The solvent used in the present invention is not particularly limited, as long as it is capable of dissolving or dispersing ethyl cellulose in the formulation. The solvent is preferably a plasticizer that is a liquid around room temperature. As such a solvent, at least one selected from the group consisting of esters, alcohols, nitrogen-containing compounds, terpenes, oils, ketones, ethers, and water, can be used, but examples of the solvent are not limited thereto. Specific examples of the solvent are shown below, but are not limited thereto.

(d-1) Esters

Examples of the esters may include: fatty acid monohydric alcohol esters, such as ethyl acetate, isopropyl isostearate, methyl stearate, ethyl linoleate, isopropyl linoleate, ethyl oleate, oleyl oleate, decyl oleate, isopropyl myristate, butyl myristate, myristyl myristate, octyldodecyl myristate, diethyl adipate, diisopropyl adipate, diisobutyl adipate, methyl laurate, hexyl laurate, methyl myristate, methyl caproate, isopropyl palmitate, isostearyl palmitate, diethyl sebacate, diisopropyl sebacate, cetyl 2-ethylhexanoate (cetyl isooctanoate), hexadecyl isostearate, butyl acetate, and benzyl acetate; aromatic carboxylic acid monohydric alcohol esters, such as diethyl phthalate, dibutyl phthalate, and triethyl citrate; lactic acid esters, such as ethyl lactate, cetyl lactate, and myristyl lactate; carbonic acid esters, such as ethylene carbonate, and propylene carbonate; and triacyl glycerol esters, such as triacetin, tricaprylin, a tri(caprylic/capric acid)glyceride-tristearic acid glyceride mixture, and tri(caprylic/capric acid)glycerin.

(d-2) Alcohols

Examples of the alcohols may include: aliphatic alcohols, such as isostearyl alcohol, isopropanol, ethanol, lauryl alcohol, 2-octyldodecanol, 2-hexyldecanol, oleyl alcohol, ethylene glycol, triethylene glycol, propylene glycol, dipropylene glycol, 1,3-butanediol, 1,2,6-hexanetriol, 2-ethyl-1,3-hexanediol, glycerin, geraniol, propylene glycol monocaprylate, diethylene glycol monoethyl ether, and polyethylene glycol; aromatic alcohols, such as glycol salicylate and benzyl alcohol.

(d-3) Nitrogen-Containing Compounds

Examples of the nitrogen-containing compound may include: aliphatic amines, such as 2-aminoethanol, ethylenediamine, diethanolamine, and triethanolamine; and amide compounds, such as N-methyl-2-pyrrolidone, lauryl pyrrolidone, and crotamiton.

(d-4) Terpenes

Examples of the terpenes may include squalane, squalene, menthol, and borneol.

(d-5) Oils

Examples of the oils may include liquid paraffin, castor oil, sesame oil, olive oil, peppermint oil, soybean oil, and eucalyptus oil.

(d-6) Ketones

An example of the ketones may be acetone.

(d-7) Ethers

Examples of the ethers may include diethyl ether and dimethyl ether.

(d-8) Others

An example of other solvents may be water.

The content of the solvent is not particularly limited, as long as it does not impair the form of the formulation.

The formulation of the present invention contains 0.1 part by weight or more of the solvent, with respect to 1 part by weight of the ethyl cellulose. The formulation of the present invention contains the solvent in an amount of preferably 0.5 parts by weight or more, and more preferably 1 part by weight or more, with respect to 1 part by weight of the ethyl cellulose, and the formulation of the present invention may contain the solvent in an amount of 2 parts by weight or more, 5 parts by weight or more, 7 parts by weight or more, or 9 parts by weight or more, with respect to 1 part by weight of the ethyl cellulose.

The formulation of the present invention contains the solvent in an amount of preferably 100 parts by weight or less, more preferably 90 parts by weight or less, and the formulation of the present invention may contain the solvent in an amount of 80 parts by weight or less, or 70 parts by weight or less, with respect to 1 part by weight of ethyl cellulose.

When the formulation of the present invention is a film-forming formulation, in order to achieve both easy applicability and the prompt formation of a film, the lower limit of the content of the solvent in the formulation of the present invention is preferably 3 parts by weight or more, more preferably 3.5 parts by weight or more, even more preferably 4 parts by weight or more, further preferably 4.5 parts by weight or more, and still further preferably 5 parts by weight or more, with respect to 1 part by weight of the ethyl cellulose. On the other hand, the upper limit of the content of the solvent in the formulation of the present invention is preferably 70 parts by weight or less, more preferably 50 parts by weight or less, even more preferably 50 parts by weight or less, further preferably 30 parts by weight or less, and still further preferably 10 parts by weight or less, with respect to 1 part by weight of the ethyl cellulose.

Moreover, the lower limit of the content of the solvent to the total amount of the formulation components is preferably 1% by weight or more, and may also be 5% by weight or more, 10% by weight or more, 20% by weight or more, 30% by weight or more, 40% by weight or more, 50% by weight or more, or 60% by weight or more. The upper limit of the content of the solvent to the total amount of the formulation components is preferably 90% by weight or less, and may also be 85% by weight or less, or 80% by weight or less.

The solvent may be used alone, or two or more types of the solvents may be mixed and may be then used.

(e) Surfactant

A surfactant may be added to the formulation of the present invention. When the present invention is applied as a film-forming formulation, a surfactant is added to the formulation comprising ethyl cellulose, so that a film-forming formulation, the surface of which is not sticky after the solidification thereof, and which has sufficient agglutination after the solidification thereof and can be easily peeled without being washed, can be realized. The surfactant is not particularly limited, as long as it has a hydrophilic group and a hydrophobic group in a single molecule or it forms a micelle in the solvent. Examples of the surfactant may include those listed as surfactants in the website of Japan Surfactant Industry Association (http://www.jp-surfactant.jp/index.html), and those classified into surfactants in Japanese Pharmaceutical Excipients Directory 2016 (edited by International Pharmaceutical Excipients Council (IPEC) Japan). The surfactant can be classified into a nonionic surfactant, an anionic surfactant, a cationic surfactant, or an amphoteric surfactant. In addition, the surfactant can also be classified into those having a glycerin skeleton or a propylene glycol skeleton, or those having a sorbitan skeleton. The N-coconut oil fatty acid acyl-L-arginine ethyl DL-pyrrolidonecarboxylic acid salt used in the after-mentioned Examples is one example of the cationic surfactant.

The surfactant may be used alone, or two or more types of the surfactants may be mixed and may be then used.

When such a surfactant is added to the formulation of the present invention, the content of the surfactant to the total amount of the formulation components is preferably 0.01% by weight or more and less than 30% by weight, more preferably 0.1% by weight or more and 25% by weight or less, further preferably 1% by weight or more and 20% by weight or less, particularly preferably 1% by weight or more and 15% by weight or less, and most preferably 1% by weight or more and 10% by weight or less, with respect to the total amount of the formulation components.

(f) Other Components

The formulation of the present invention may comprise organic acid, a dissolving agent, and the like, as necessary.

Examples of the organic acid may include: fatty acids, such as citric acid, adipic acid, isostearic acid, caprylic acid, capric acid, acetic acid, stearic acid, lactic acid, palmitic acid, propionic acid, fumaric acid, behenic acid, maleic acid, and myristic acid; and aromatic carboxylic acids, such as benzoic acid, phthalic acid, and salicylic acid. Examples of the dissolving agent may include butyl stearate, methyl palmitate, cetyl palmitate, retinol palmitate, cetanol, myristyl alcohol, diisopropanolamine, triisopropanolamine, urea, cysteine, and methionine.

The organic acid or the dissolving agent may be used alone or in combination of two or more types. The formulation may comprise the organic acid or the dissolving agent in a range that does not impair the form of the formulation. Among others, the content of the organic acid or the dissolving agent is preferably 20% by weight or less, more preferably 15% by weight or less, further preferably 10% by weight or less, and particularly preferably 7% by weight or less, with respect to the total amount of the formulation components.

When the organic acid or the dissolving agent is used, the organic acid or the dissolving agent can be added to the formulation by being replaced with a part of any component constituting the formulation.

The formulation according to the present invention may be produced by further adding thereto various types of known additives, namely, stabilizers, antioxidants, bases, thickeners, solubilizers, buffers, absorption promoters, binders, suspending agents, coating agents, fillers, softeners, adhesives, tackifiers, thickeners, pH regulators, excipients, dispersants, disintegrants, antiseptics, dissolving agents, perfumes, coloring agents, preservatives, and the like, as long as these additives do not impair the effects of the present invention.

[Form of Formulation]

The formulation of the present invention is preferably an external formulation, such as, for example, a liquid formulation, a semi-solid formulation, or a patch. The formulation of the present invention is more preferably a liquid formulation or a semi-solid formulation. The formulation of the present invention may also be a film-forming formulation that is solidified after being applied to an affected area.

As an example, the formulation of the present invention can be used as a nail-coating agent.

As an example, when the formulation of the present invention contains efinaconazole or a salt thereof, it can be used as a therapeutic agent for nail trichophytosis.

[Method for Producing Formulation]

When the present invention is applied as a film-forming formulation, the formulation can be produced by mixing and stirring the following components. That is to say, (a) an active pharmaceutical ingredient, (b) ethyl cellulose, (c) 2-mercaptobenzimidazole, and (d) a solvent are mixed with one another, and the obtained mixture is then stirred, so that the formulation can be obtained. Regarding the order of mixing the components, for example, the above-described components (a) to (d) may be added simultaneously, or the above-described components (b) to (d) may be mixed in any given order, and the above component (a) may be then added thereto. Individual components may be prepared in a formulation storage container, or the components may be prepared in each different containers and may be then transferred into the storage container.

In order to homogeneously mix the components with one another, the components may be heated during the mixing and stirring thereof. In order to prevent degeneration or volatilization of the formulation components, the upper limit of the temperature is preferably 100° C. or lower, and more preferably 90° C. or lower.

EXAMPLES

The present invention will be more specifically described in the following examples, comparative examples, test examples, and formulation examples. However, the present invention is not limited to these examples.

The numerical value of each component shown in Tables indicates "part by weight."

BHT: di-tert-butylhydroxytoluene

CAE (registered trademark): N-coconut oil fatty acid acyl-L-arginine ethyl DL-pyrrolidonecarboxylic acid salt Example 1

Efinaconazole (10 parts by weight), ethyl cellulose (N100 Pharm, 10 parts by weight), CAE (registered trademark) (1.5 parts by weight), BHT (1 part by weight), 2-mercaptobenzimidazole (1 part by weight), citric acid (2 parts by weight), and ethanol (94.5 parts by weight) were mixed with one another to prepare a sample (total amount: 2.2 g). Each components and the weights thereof (part by weight) are shown in Table 1.

Comparative Example 1

A sample (total amount: 2.2 g) was prepared in the same manner as that of Example 1, with the exception that 2-mercaptobenzimidazole was not used. Each components and the weights thereof (part by weight) are shown in Table 1.

The amount of impurities was evaluated based on the ratio (%) of the peak area of impurities to the peak area of efinaconazole in HPLC (high performance liquid chromatography). The analysis method of HPLC is as follows. The amount of impurities is shown in Table 1.

(Analysis Method of HPLC)

Approximately 25 mg of specimen is taken, and is then dispersed in a mixed solution of an eluent with the following composition (approx. 4 mL) and ethanol (approx. 0.3 mL).

The obtained solution is filtrated through a membrane filter (manufactured by Toyo Roshi Kaisha, Ltd., DISMIC 13HP045AN) to obtain a measurement specimen.

The obtained specimen is measured according to HPLC under the following conditions.

HPLC: SHIMAZU LC-2010HT

Eluent: 0.1% $H_3PO_4$ aqueous solution/$CH_3CN$/sodium lauryl sulfate=600 mL/400 mL/0.9 g Flow rate: 1 mL/min Wavelength: 215 nm Injected amount: 10 µL Measurement time: 35 min Column: Phenomenex 00D-4251-E0, Luna 3 µm C18(2), 100×4.60 mm Column temperature: 40° C.

TABLE 1

| | Example 1 | Comparative Example 1 | Comparative Example 2 | Comparative Example 3 | Comparative Example 4 | Comparative Example 5 | Comparative Example 6 |
|---|---|---|---|---|---|---|---|
| Efinaconazole | 10 | 10 | 10 | 10 | 10 | 10 | 10 |
| Ethyl cellulose | 10 | 10 | 10 | 10 | 10 | 10 | 10 |
| CAE (registered trademark) | 1.5 | 1.5 | 1.5 | 1.5 | 1.5 | 1.5 | 1.5 |
| BHT | 1 | 1 | 1 | 1 | 1 | 1 | 1 |
| Citric acid | 2 | 2 | 2 | 2 | 2 | 2 | 2 |
| 2-Mercapto benzimidazole | 1 | | | | | | |
| 1,2,3-Benzotriazole | | | 1 | | | | |
| Urea | | | | 1 | | | |
| Tocopheryl acetate | | | | | 1 | | |
| 1,3-Butylene glycol | | | | | | 1 | |
| Soy lecithin | | | | | | | 1 |
| Ethanol | 94.5 | 94.5 | 94.5 | 94.5 | 94.5 | 94.5 | 94.5 |
| Amount of impurities (%) | 0 | 0.1 | 0.15 | 0.13 | 0.18 | 0.14 | 0.2 |

Comparative Examples 2 to 6

A sample (total amount: 2.2 g) was prepared in the same manner as that of Example 1, with the exception that 1,2,3-benzotriazole, urea, tocopheryl acetate, 1,3-butylene glycol, or soy lecithin was used instead of 2-mercaptobenzimidazole. Each components and the weights thereof (part by weight) are shown in Table 1.

Test Example 1

The sample prepared in each of Example 1 and Comparative Examples 1 to 6 was stirred using ChemiStation manufactured by EYELA at an outside temperature of 70° C. at 230 rpm for 2 days. The present test was carried out as a stress testing for confirming the stability of the quality of the formulation during the long-term storage.

As shown in Table 1, in Example 1 in which 2-mercaptobenzimidazole was used, generation of impurities could be almost completely suppressed in the 70° C. stress testing.

Examples 2 to 4

The components shown in Table 2 were mixed with one another in the amounts shown in Table 2, to prepare a sample (total amount: 2.2 g).

Test Example 2

Using the sample prepared in each of Examples 2 to 4, the amount of impurities was evaluated in the same manner as that of Test Example 1. The amount of impurities is shown in Table 2.

TABLE 2

|  | Example 2 | Example 3 | Example 4 |
|---|---|---|---|
| Efinaconazole | 10 | 10 | 10 |
| Ethyl cellulose | 10 | 10 | 10 |
| CAE (registered trademark) | 1.5 | 1.5 | 1.5 |
| BHT |  | 1 |  |
| Citric acid |  |  | 2 |
| 2-Mercaptobenzimidazole | 1 | 1 | 1 |
| Ethanol | 97.5 | 96.5 | 95.5 |
| Amount of impurities (%) | 0.016 | 0.009 | 0 |

As shown in Table 2, in Examples 2 to 4 in which 2-mercaptobenzimidazole was used, generation of impurities could be sufficiently suppressed in the 70° C. stress testing, regardless of the use or non-use of BHT and citric acid.

Examples 5 to 7

The components shown in Table 3 were mixed with one another in the amounts shown in Table 3, to prepare a sample (total amount: 2.2 g).

Test Example 3

Using the sample prepared in each of Examples 5 to 7, the amount of impurities was evaluated in the same manner as that of Test Example 1. The amount of impurities is shown in Table 3.

TABLE 3

|  | Example 5 | Example 6 | Example 7 |
|---|---|---|---|
| Efinaconazole | 10 | 10 | 10 |
| Ethyl cellulose | 10 | 10 | 10 |
| CAE (registered trademark) | 1.5 | 1.5 | 1.5 |
| Citric acid | 1 | 0.4 | 0.2 |
| 2-Mercaptobenzimidazole | 0.5 | 0.2 | 0.1 |
| Ethanol | 97 | 97.9 | 98.2 |
| Amount of impurities (%) | 0 | 0.009 | 0.015 |

As shown in Table 3, in Examples 5 to 7 in which 2-mercaptobenzimidazole was used, generation of impurities could be sufficiently suppressed in the 70° C. stress testing, even in a case where the content of 2-mercaptobenzimidazole was changed.

Examples 8 to 10 and Comparative Examples 7 to 9

The components shown in Table 4 were mixed with one another in the amounts shown in Table 4, to prepare a sample (total amount: 1.0 g). It is to be noted that the formulations of Examples 8 and 10 and Comparative Examples 7 and 9 were semi-solid formulations, whereas the formulations of Example 9 and Comparative Example 8 were liquid formulations.

Example 11

Efinaconazole (10 parts by weight), ethyl cellulose (manufactured by Ashland, N100 Pharm, 60 parts by weight), 2-mercaptobenzimidazole (1 part by weight), 2-hexyldecanol (29 parts by weight), and ethanol (240 parts by weight) were mixed with one another to prepare a formulation solution (total amount: 17 g). Using an applicator, the obtained formulation solution was coated onto a polyethylene terephthalate (PET) film with a thickness of 80 µm, the surface of which had been treated with silicon, and thereafter, ethanol was removed by drying the film in a hot air oven at 50° C. for 1 hour. To the surface of the obtained dried matter, another PET film was attached, so as to obtain a solid formulation, both sides of which were sandwiched with the PET films. Each components and the weights thereof (part by weight) are shown in Table 4.

Comparative Example 10

A solid formulation was prepared in the same manner as that of Example 11, with the exceptions that 2-mercaptobenzimidazole was not added, and that the amount of 2-hexyldecanol was changed as shown in Table 4. Each components and the weights thereof (part by weight) are shown in Table 4.

Test Example 4

The sample prepared in each of Examples 8 to 10 and Comparative Examples 7 to 9 was placed in a 9-mL glass vial, and the glass vial was then enclosed with a wrapping film (manufactured by Fujimori Kogyo Co., Ltd., NI-β), which was then preserved in a constant-temperature stability testing machine under conditions of 40° C./75% RH for 12 days. The sample prepared in each of Example 11 and Comparative Example 10 was not placed in the glass vial, but was directly enclosed with a wrapping film (manufactured by Fujimori Kogyo Co., Ltd., NI-(3), which was then preserved in a constant-temperature stability testing machine under conditions of 40° C./75% RH for 12 days. The present test was carried out as an accelerated test for confirming the stability of the quality of the formulation during the long-term storage.

The amount of impurities was evaluated based on the ratio (%) of the peak area of specific impurities (relative retention time=0.63) to the peak area of efinaconazole in HPLC (high performance liquid chromatography). It is to be noted that efinaconazole has a cyclic tertiary amine structure, a nitrogen-containing aromatic ring structure (triazole), and an open-chain tertiary alcohol structure.

(Analysis Method of HPLC)

The analysis method of HPLC was carried out in the same manner as that described above, with the exception that the specimen was taken so that the amount of the drug became approximately 2.5 mg. The amount of impurities is shown in Table 4

TABLE 4

|  | Example 8 | Example 9 | Example 10 | Example 11 | Comparative Example 7 | Comparative Example 8 | Comparative Example 9 | Comparative Example 10 |
|---|---|---|---|---|---|---|---|---|
| Efinaconazole | 10 | 20 | 0.5 | 10 | 10 | 20 | 0.5 | 10 |
| Ethyl cellulose | 10 | 1 | 20 | 60 | 10 | 1 | 20 | 60 |
| 2-Mercapto Benzimidazole | 1 | 2 | 2 | 1 | | | | |
| 2-Hexyldecanol | | | | 29 | | | | 30 |
| Ethanol | 79 | 77 | 77.5 | | 80 | 79 | 79.5 | |
| Amount of impurities (%) | 0 | 0 | 0 | 0 | 0.21 | 0.05 | 0.79 | 1.93 |

As shown in Table 4, in Examples 8 to 11 in which 2-mercaptobenzimidazole was used, generation of impurities could be completely suppressed in the 40° C./75% RH accelerated test, even though the content of the active pharmaceutical ingredient, the content of the ethyl cellulose, the content of the 2-mercaptobenzimidazol, and the content of the solvent were changed.

Examples 12 and 13 and Comparative Examples 11 and 12

The components shown in Table 5 were mixed with one another in the amounts shown in Table 5, to prepare a sample (total amount: 1.0 g).

Test Example 5

Using the sample prepared in each of Examples 12 and 13 and Comparative Examples 11 and 12, the amount of impurities in the sample was evaluated in the same manner as that of Test Example 4. The amount of impurities is shown in Table 5.

TABLE 5

|  | Example 12 | Example 13 | Comparative Example 11 | Comparative Example 12 |
|---|---|---|---|---|
| Efinaconazole | 10 | 10 | 10 | 10 |
| Ethyl cellulose | 10 | 10 | 10 | 10 |
| 2-Mercaptobenzimidazole | 1 | 1 | | |
| Ethanol | | 69 | | 70 |
| Isopropanol | 79 | | 80 | |
| Propylene glycol | 4 | | 4 | |
| Propylene glycol monocaprylate | 2 | | 2 | |
| Diisopropyl adipate | | 2 | | 2 |
| Water | | 2 | | 2 |
| Amount of impurities (%) | 0 | 0 | 0.37 | 0.26 |

As shown in Table 5, in Examples 12 and 13 in which 2-mercaptobenzimidazole was used, generation of impurities could be completely suppressed in the 40° C./75% RH accelerated test, even though various solvents other than ethanol were used.

Examples 14 to 17 and Comparative Examples 13 to 16

The components shown in Table 6 were mixed with one another in the amounts shown in Table 6, to prepare a sample (total amount: 1.0 g).

Test Example 6

Using the sample prepared in each of Examples 14 to 17 and Comparative Examples 13 to 16, the amount of impurities in the sample was evaluated in the same manner as that of Test Example 4. It is to be noted that the relative retention time of specific impurities in each drug under the above-described HPLC analysis conditions was as follows: ritodrine=0.63, clonidine=0.76, granisetron=0.96, and prednisolone=2.97. The amount of impurities is shown in Table 6.

TABLE 6

|  | Example 14 | Example 15 | Example 16 | Example 17 | Comparative Example 13 | Comparative Example 14 | Comparative Example 15 | Comparative Example 16 |
|---|---|---|---|---|---|---|---|---|
| Ritodrine hydrochloride | 1 | | | | 1 | | | |
| Clonidine | | 10 | | | | 10 | | |
| Granisetron | | | 1 | | | | 1 | |
| Prednisolone | | | | 1 | | | | 1 |
| Ethyl cellulose | 10 | 10 | 10 | 10 | 10 | 10 | 10 | 10 |
| Diethanolamine | 10 | | | | 10 | | | |
| 2-Mercaptobenzimidazole | 1 | 1 | 1 | 1 | | | | |
| Ethanol | 78 | 79 | 88 | 88 | 79 | 80 | 89 | 89 |
| Amount of impurities (%) | 0.16 | 0.003 | 0.01 | 0.04 | 0.87 | 0.01 | 0.1 | 0.11 |

As shown in Table 6, in Examples 14 to 17 in which 2-mercaptobenzimidazole was used, an increase in the amount of specific impurities was significantly suppressed in the case of using ritodrine hydrochloride having an open-chain alcohol structure, a cyclic alcohol structure and an open-chain secondary amine structure, clonidine having an imine structure and a cyclic secondary amine structure, granisetron having a cyclic tertiary amine structure, an open-chain secondary amine structure and a nitrogen-containing aromatic ring structure (pyrazole), and prednisolone having a cyclic carbonyl structure, an open-chain carbonyl structure, a cyclic alcohol structure and an open-chain alcohol structure.

Examples 18 to 20 and Comparative Examples 17 to 19

The components shown in Table 7 were mixed with one another in the amounts shown in Table 7, to prepare a sample (total amount: 2.2 g).

Test Example 7

Using the sample prepared in each of Examples 18 to 20 and Comparative Examples 17 to 19, the amount of individual specific impurities was evaluated in the same manner as that of Test Example 1 (a stress testing at 70° C. for 2 days). The relative retention time of specific impurities in donepezil under the above-described HPLC analysis conditions was 1.11. In the case of ketoconazole and itraconazole, the test was carried out in the same manner as that of Test Example 1, with the exception that the eluent used in HPLC was set to be a 0.1% $H_3PO_4$ aqueous solution/$CH_3CN$/MeOH/sodium lauryl sulfate=400 mL/500 mL/100 mL/0.9 g. The relative retention time of specific impurities was as follows: ketoconazole=1.19, and itraconazole=0.82. The amount of impurities is shown in Table 7.

TABLE 7

| | Example 18 | Example 19 | Example 20 | Comparative Example 17 | Comparative Example 18 | Comparative Example 19 |
|---|---|---|---|---|---|---|
| Donepezil | 10 | | | 10 | | |
| Ketoconazole | | 10 | | | 10 | |
| Itraconazole | | | 10 | | | 10 |
| Ethyl cellulose | 10 | 10 | 10 | 10 | 10 | 10 |
| 2-Mercapto benzimidazole | 1 | 1 | 1 | | | |
| Ethanol | 90 | 90 | 90 | 90 | 90 | 90 |
| Amount of impurities (%) | 0 | 0 | 0 | 0.15 | 1.38 | 0.35 |

As shown in Table 7, in Examples 18 to 20 in which 2-mercaptobenzimidazole was used, an increase in the amount of specific impurities was significantly suppressed in the case of using donepezil having an open-chain ether structure, a cyclic carbonyl structure and a cyclic tertiary amine structure, ketoconazole having a cyclic ether structure, an open-chain carbonyl structure, a cyclic tertiary amine structure and a nitrogen atom in an aromatic ring, and itraconazole having a cyclic ether structure, an open-chain ether structure, a cyclic carbonyl structure, a cyclic tertiary amine structure and a nitrogen atom in an aromatic ring.

The invention claimed is:
1. A formulation comprising:
   (a) an active pharmaceutical ingredient,
   (b) ethyl cellulose,
   (c) 2-mercaptobenzimidazole, and
   (d) 0.1 part by weight or more of solvent with respect to 1 part by weight of the ethyl cellulose, wherein
   the content of the active pharmaceutical ingredient is 0.1% by weight or more and 30% by weight or less,
   the content of the ethyl cellulose is 0.1% by weight or more and 60% by weight or less,
   the content of the 2-mercaptobenzimidazole is 0.5% by weight or more and 10% by weight or less, and
   wherein the active pharmaceutical ingredient is a compound having a cyclic tertiary amine structure, Ritodrine hydrochloride, Clonidine, Granisetron, or Prednisolone.

2. The formulation according to claim 1, wherein the content of the solvent is 1% by weight or more and 90% by weight or less.

3. The formulation according to claim 1, wherein the active pharmaceutical ingredient is a nitrogen atom-containing compound.

4. The formulation according to claim 1, wherein the active pharmaceutical ingredient is efinaconazole or a salt thereof.

5. The formulation according to claim 1, wherein the active pharmaceutical ingredient is an oxygen atom-containing compound.

6. The formulation according to claim 5, wherein the oxygen atom-containing compound is a compound comprising a hydroxyl group, a carbonyl group, or an ether group.

7. The formulation according to claim 5, wherein the oxygen atom-containing compound is a compound comprising a cyclic alcohol structure, a cyclic carbonyl structure or a cyclic ether structure.

8. The formulation according to claim 1, wherein the active pharmaceutical ingredient is a sulfur atom-containing compound.

9. The formulation according to claim 1, further comprising organic acid.

10. The formulation according to claim 1, wherein the solvent is at least one solvent selected from the group consisting of esters, alcohols, nitrogen-containing compounds, terpenes, oils, ketones, ethers, and water.

11. The formulation according to claim 1, wherein the solvent is at least one solvent selected from the group consisting of ethanol, isopropanol, ethyl acetate, water, isopropyl myristate, octyldodecyl myristate, diisopropyl adipate, diethyl sebacate, cetyl 2-ethylhexanoate (cetyl isooctanoate), hexadecyl isostearate, triethyl citrate, isostearyl alcohol, lauryl alcohol, 2-octyldodecanol, 2-hexyldecanol, oleyl alcohol, propylene glycol, 1,3-butanediol, propylene glycol monocaprylate, diethylene glycol monoethyl ether, polyethylene glycol, N-methyl-2-pyrrolidone, and liquid paraffin.

12. The formulation according to claim 1, wherein the formulation is a liquid formulation or a semi-solid formulation.

13. The formulation according to claim 12, 2-mercaptobenzimidazole is 0.5% a film-forming formulation that is solidified after being applied to an affected area.

* * * * *